(12) United States Patent
Mun et al.

(10) Patent No.: US 10,935,545 B2
(45) Date of Patent: Mar. 2, 2021

(54) SIMULTANEOUS ANALYSIS METHOD FOR MULTIPLE TARGETS USING MULTIPLE METAL NANO-TAGS

(71) Applicant: SLSBIO CO., LTD., Suwon-si (KR)

(72) Inventors: Hae Ran Mun, Seongnam-si (KR); Jong Su Kim, Seongnam-si (KR); Inae Kim, Yongin-si (KR)

(73) Assignee: SLSBIO CO., LTD.

( * ) Notice: Subject to any disclaimer, the term of this patent is extended or adjusted under 35 U.S.C. 154(b) by 167 days.

(21) Appl. No.: 15/573,506

(22) PCT Filed: May 13, 2016

(86) PCT No.: PCT/KR2016/005116
§ 371 (c)(1),
(2) Date: Nov. 13, 2017

(87) PCT Pub. No.: WO2016/182402
PCT Pub. Date: Nov. 17, 2016

(65) Prior Publication Data
US 2018/0143184 A1  May 24, 2018

(30) Foreign Application Priority Data
May 13, 2015  (KR) .................. 10-2015-0066820

(51) Int. Cl.
*G01N 33/532* (2006.01)
*G01N 33/553* (2006.01)
(Continued)

(52) U.S. Cl.
CPC ............. *G01N 33/532* (2013.01); *C12Q 1/70* (2013.01); *G01N 27/62* (2013.01);
(Continued)

(58) Field of Classification Search
CPC ..... G01N 33/532; G01N 33/543; G01N 33/553
See application file for complete search history.

(56) References Cited

U.S. PATENT DOCUMENTS 8,481,115 B2    7/2013  Tokoro et al.
2003/0059955 A1*  3/2003  Bamdad ............... G01N 33/588
506/9

(Continued)

FOREIGN PATENT DOCUMENTS

KR       20140098285 A      8/2014
WO        2007137418 A1    12/2007
WO      WO2014030985 A1 *   2/2014

OTHER PUBLICATIONS

Zhang et al. ("Magnetic immunoassay coupled with inductively coupled plasma mass spectrometry for simultaneous quantification of alpha-fetoprotein and carcinoembryonic antigen in human serum", Spectrochimica Acta Part B, vol. 106, pp. 20-27, published Feb. 2, 2015) (Year: 2015).*

(Continued)

*Primary Examiner* — Tracy Vivlemore
*Assistant Examiner* — Nam P Nguyen
(74) *Attorney, Agent, or Firm* — Dilworth IP, LLC

(57) ABSTRACT

The present invention relates to a simultaneous analysis method for a target using a plurality of metal nano-tags and, more particularly, to a simultaneous analysis method for a target using a plurality of metal nano-tags, wherein the method fuses a nano-particle technology on the basis of an antigen-antibody reaction, which is a conventional biological immune response, and simultaneously diagnoses a plurality of target materials by using a plurality of antigen-antibody reactions and a plurality of metal nano-tags, thereby enhancing diagnostic effect.

5 Claims, 2 Drawing Sheets

(51) Int. Cl.
*G01N 33/543* (2006.01)
*C12Q 1/70* (2006.01)
*G01N 27/62* (2021.01)
*G01N 33/68* (2006.01)
*G01N 33/576* (2006.01)
*G01N 33/569* (2006.01)
*G01N 33/552* (2006.01)
*G01N 33/58* (2006.01)
*C01G 7/00* (2006.01)

(52) U.S. Cl.
CPC . *G01N 33/54333* (2013.01); *G01N 33/54346* (2013.01); *G01N 33/552* (2013.01); *G01N 33/553* (2013.01); *G01N 33/569* (2013.01); *G01N 33/5761* (2013.01); *G01N 33/587* (2013.01); *G01N 33/6848* (2013.01); *C01G 7/00* (2013.01); *C01P 2004/64* (2013.01); *G01N 2458/15* (2013.01)

(56) References Cited

U.S. PATENT DOCUMENTS

| | | | |
|---|---|---|---|
| 2005/0218319 A1 | 10/2005 | Bandura et al. | |
| 2014/0308756 A1 | 10/2014 | Gautier et al. | |
| 2015/0038347 A1 | 2/2015 | Johnson et al. | |
| 2015/0219640 A1* | 8/2015 | Lim | G01N 33/54313 435/5 |

OTHER PUBLICATIONS

Choi et al. (Analytical Chimica Acta, vol. 847, pp. 10-15, published Aug. 21, 2014) (Year: 2014).*
Zhang et al. (Spectrochimica Acta Part B 106 (2015) 12-27, published Feb. 2, 2015). (Year: 2015).*
Gong et al. (Biosensors and Bioelectronics, vol. 22, pp. 1501-1507, published Sep. 12, 2006). (Year: 2006).*
Gong et al., Biosensors and Bioelectronics, 2007, vol. 22, No. 7, pp. 1501-1507.
Wu et al., Biosensors and Bioelectronics, 2011, vo. 30, No. 1, pp. 34-42.
PCT International Search Report and Written Opinion dated Aug. 9, 2016 from corresponding Application No. PCT/KR2016/005116, 16 pages.
Jung Aa Ko, et al., "Metal/Dye-Doped Core-Shell Silica Nanoparticles for Potential Use in Bioassay"; J. Anal. At. Spectrom., 2013, 28, pp. 630-636.
O. Ornatsky, et al.; "Multiple Cellular Antigen Detection by ICP-MS"; Journal of Immunological Methods 308 (2006) pp. 68-76.
Rui Liu, et al.; "Sensitive Sandwich Immunoassay Based on Single Particle Mode Inductively Coupled Plasma Mass Spectrometry Detection"; Talanta 83 (2010) pp. 48-54.
Sichun Zhang, et al.; "Simultaneous Determination of α-Fetoprotein and Free β-Human Chorionic Gonadotropin by Element-Tagged Immunoassay with Detection by Inductively Coupled Plasma Mass Spectrometry"; Clinical Chemistry 50:7, pp. 1214-1221 (2004).
Supplementary European Search Report; Application No. EP 16 79 3048; dated Nov. 28, 2018; 9 pages.

* cited by examiner

HBV result

HIV result

SIMULTANEOUS ANALYSIS METHOD FOR MULTIPLE TARGETS USING MULTIPLE METAL NANO-TAGS

BACKGROUND OF THE INVENTION

Field of the Invention

The present invention relates to a method for simultaneous analysis of a target using a plurality of metal nano-tags and, more particularly, to a method for simultaneous analysis of a target using a plurality of metal nano-tags, in which the method allows the convergence of a nano-particle technology based on an antigen-antibody reaction, which is a conventional biological immune response, and simultaneously diagnoses a plurality of target materials using a plurality of antigen-antibody reactions and a plurality of metal nano-tags, thereby enhancing diagnostic effect.

Related Art

Major pathogenic viruses, for example, hepatitis B virus (HBV), hepatitis C virus (HCV), and human immunodeficiency virus (HIV), which are spread through blood or body fluids, are very important prognostic factors in blood management for transfusion.

Currently, the infection diagnosis of these pathogens is mainly performed by an enzyme-linked immunosorbent assay (ELISA), which can detect the presence of HBV surface antigen (HBsAg) or antibodies against HCV and HIV in the blood and thereby determine the presence of virus infection. However, ELISA has a problem in that the accuracy of the assay is low during the latent period until the antibody is formed after virus infection, while it is in a state of infection of viruses with different immune activities, or immune inactivity of the infected person.

In order to overcome the limitations of ELISA, a method that has been developed over the past several years is a nucleic acid test (NAT) which directly detects a genetic material of a virus consisting of DNA or RNA. The nucleic acid test is a diagnostic method for analyzing the presence/absence of a virus with enhanced sensitivity compared to enzyme immunoassay, using an oligo primer with nucleotide sequence specificity for viral nucleic acid. The nucleic acid test was expected to be appropriately utilized for screening pathogenic viruses that are transmitted through the blood in the fields of blood-associated business such as blood transfusion or biopharmaceutical business. However, it is difficult to utilize the nucleic acid test as a routine test method to handle a large amount of specimens due to the problem of cost incurring in the course of introducing and utilizing the test method.

In addition, there is a method called "multiplex NAT" to be used as a method for simultaneously detecting several kinds of viruses. The multiplex NAT has the effect of reducing the inspection time and effort to some extent if introduced. However, the method has difficulties in that the sensitivity may be degraded unless the optimization of the reaction conditions is warranted and that there is a risk of false positive or false negative, and also there is still difficulty in terms of inspection costs to utilize the method as a routine test method to handle a large amount of specimens.

Despite the advantages and disadvantages of various methods for the diagnosis of viruses as described above, the technology primarily used in clinical diagnostics at present to detect viruses is ELISA based on antigen-antibody reaction. Although ELISA method is commonly used because the operation of the measuring machine is simple and the sample can be processed rapidly, the assay has many problems in that the types of usable chromogens or phosphors are limited, there is a difficulty in tagging, reactivity of enzymes related to color development, and in the case of fluorescence, there are various constraints for measurements due to photo bleaching, quenching, etc. In particular, it is even more so in the field of applications where quantitative measurements are required.

Accordingly, there is a need for the development of a novel technology that enables accurate measurement and quantification as well as quantification of target materials such as various kinds of proteins in various matrices.

For this purpose, there is known a method which can detect even a trace amount of virus by using metal nano-tags instead of phosphors or other chromogenic compounds in the conventional ELISA method and measuring the mass of the metal.

However, conventionally, the method using a metal nano-tag has a problem in that it is difficult to simultaneously detect a plurality of targets because it includes only one kind of metal.

SUMMARY OF THE INVENTION

In order to solve the problems in the conventional technologies, an object of the present invention is to provide a novel method of analysis which enables simultaneous analysis of a plurality of targets using a plurality of antibodies.

The present invention, in order to solve the above objects, provides a method for simultaneous analysis of a plurality of targets using a plurality of metal nano-tags, which includes:

(i) preparing an analysis platform to which a first antibody, that specifically binds to a target, is bound;

(ii) reacting the analysis platform including the first antibody with a sample containing a plurality of targets and thereby forming an analysis platform to which target materials are bound;

(iii) reacting a second antibody, that specifically binds to a target, with the analysis platform in which the first antibody and targets are bound; and (iv) performing a quantitative analysis of the material to which the second antibody is bound.

In the method for simultaneous analysis of targets using a plurality of metal nano-tags according to the present invention, the target molecule to be analyzed may be a biomolecule. The biomolecule is a material that is released or separated in vivo and it may include not only materials generated in vivo, but also materials put into a living body and remain therein for a predetermined time. For example, biomolecules can include antibiotics, nucleic acids, hormones, enzymes, cells, tumors, cancer cells, bacteria, viruses, secretions thereof, etc. Examples of the antibiotics may include salinomycin, enrofloxacin, ciprofloxacin, penicillin, cephalosporin, carbapenem, ampicillin, neomycin, gentamicin, isepamicin, sisomicin, erythromycin, clarithromycin, vancomycin, teicoplanin, lincomycin, sulfathiazole, tetracycline, oxytetracycline, sulfamerazine, etc., and examples of cell secretions may include prostate-specific antigens, which are proteins synthesized in prostate cells, but the antibiotics and cell secretions are not limited thereto.

In the method for simultaneous analysis of targets using a plurality of metal nano-tags by the present invention, the analysis platform to which the first antibody is bound is characterized by containing a plurality of types of antibodies.

In the method for simultaneous analysis of targets using a plurality of metal nano-tags by the present invention, the analysis platform to which the first antibody is bound may be silica nanoparticle which contains a metal-containing core and silica that coats the surface of the core, or a plate to which a plurality of types of first antibodies are bound. In the method for simultaneous analysis of targets using a plurality of metal nano-tags by the present invention, the case of silica nanoparticle where the analysis platform to which the first antibody is bound is silica nanoparticle which contains a metal-containing core and silica that coats the surface of the core is illustrated in FIG. 1, and the case of silica nanoparticle where the analysis platform to which the first antibody is bound is a plate to which a plurality of types of first antibodies are bound is illustrated in FIG. 2.

In the method for simultaneous analysis of targets using a plurality of metal nano-tags by the present invention, each of the silica nanoparticles is characterized by containing a single kind of metal, and the analysis platform to which the antibody is bound is characterized by containing at least two types of silica nanoparticles with different types of metals. The method for simultaneous analysis of targets using a plurality of metal nano-tags by the present invention is characterized in that the method can diversify the kinds of targets according to the type of the first antibody via analysis by attaching a different type of the first antibody to a plurality of the silica nanoparticles with different types of metals, and the method also enables a simultaneous analysis of two different kinds of metals when quantitative analysis is performed later using an inductively coupled plasma mass spectrometry (ICP-MS) by varying the kinds of the metals contained in the silica nanoparticles.

In the method for simultaneous analysis of targets using a plurality of metal nano-tags by the present invention, the metals contained in the silica nanoparticles may be selected from the group consisting of Au, Ag, Pt, Pd, Ir, Rh, Ru, Al, Cu, Te, Bi, Pb, Fe, Ce, Mo, Nb, W, Sb, Sn, V, Mn, Ni, Co, Zn, La, Ce, Pr, Nd, Pm, Sm, Eu, Gd, Tb, Dy, Ho, Er, Tm, Yb, Lu, Sc, Y, and Ti.

In the method for simultaneous analysis of targets using a plurality of metal nano-tags by the present invention, the analysis platform to which the first antibody is bound is characterized by having at least two types of a plurality of types of silica nanoparticles selected from the group consisting of silica nanoparticle including silica nanoparticle containing Au, silica nanoparticle containing Gd, silica nanoparticle containing Y, and silica nanoparticle containing Eu.

In the method for simultaneous analysis of targets using a plurality of metal nano-tags by the present invention, for the analysis platform to which the first antibody is bound, an appropriate metal may be selected depending on the target to be analyzed. Specifically, silica nanoparticle containing Au is desirable when the target to be analyzed is HBV in the blood; silica nanoparticle containing Gd is desirable when the target to be analyzed is HIV in the blood; and silica nanoparticle containing Eu is desirable when the target to be analyzed is HCV in the blood; and it is possible that at least two of these silica nanoparticles are used simultaneously.

In another exemplary embodiment of the present invention, it is possible to use the conventional ELISA method as it is except that the analysis platform to which the first antibody is bound is a plate to which a plurality of types of the first antibodies are bound and that a plurality of types of the first antibodies are bound.

In the method for simultaneous analysis of targets using a plurality of metal nano-tags by the present invention, when the analysis platform is a plate to which a plurality of types of the first antibodies are bound, the second antibodies are characterized by being bound to silica nanoparticles which contain a metal-containing core and/or silica that coats the surface of the core.

In the method for simultaneous analysis of targets using a plurality of metal nano-tags by the present invention, the core of the silica nanoparticles to which the second antibodies are bound is characterized by containing at least two metals selected from the group consisting of Au, Ag, Pt, Pd, Ir, Rh, Ru, Al, Cu, Te, Bi, Pb, Fe, Ce, Mo, Nb, W, Sb, Sn, V, Mn, Ni, Co, Zn, La, Ce, Pr, Nd, Pm, Sm, Eu, Gd, Tb, Dy, Ho, Er, Tm, Yb, Lu, Sc, Y, and Ti.

In the method for simultaneous analysis of targets using a plurality of metal nano-tags by the present invention, the core of the silica nanoparticles to which the second antibodies are bound is characterized by containing Au.

In the method for simultaneous analysis of targets using a plurality of metal nano-tags by the present invention, the first antibody is characterized to be a monoclonal antibody.

In the method for simultaneous analysis of targets using a plurality of metal nano-tags by the present invention, it is possible that the first antibody and the second antibody to be used are the same.

In the method for simultaneous analysis of targets using a plurality of metal nano-tags by the present invention, it is possible that the first antibody is a monoclonal antibody and the second antibody is a polyclonal antibody.

In the method for simultaneous analysis of targets using a plurality of metal nano-tags by the present invention, step (iv) of performing a quantitative analysis of the material to which the second antibody is bound includes:

(iv-1) capturing the target material to which the second antibody is bound by applying an external magnetic force; and (iv-2) analyzing the captured target material to which the second antibody is bound using a spectrophotometer. That is, in the case of using silica nanoparticles as the analysis platform to which the first antibody is bound, the target to which the second antibody is bound is separated by the magnetism of the magnetic nanoparticles which are connected to the second antibody, and the tagged metal of the separated target to which even the second antibody is bound is subjected to quantitative analysis for the analysis of the target.

In another exemplary embodiment of the present invention, in the case of using the first antibody bound to a plate as the analysis platform to which the first antibody is bound, step (iv) of performing a quantitative analysis of the material to which the second antibody is bound is characterized in that it includes:

(iv-1) separating the material, which is bound to the first antibody of the plate, to which the second antibody is bound; and (iv-2) analyzing only the material, which is bound to the first antibody of the plate, to which the second antibody is bound using a spectrophotometer. That is, since the target to which even the second antibody is bound is fixed onto a plate, it is possible to perform a quantitative analysis for a plurality of targets by subjecting the tagged metal bound to the second antibody after the simple separation.

In the method for simultaneous analysis of targets using a plurality of metal nano-tags by the present invention, step (iv-2) of analyzing the captured target material to which the second antibody is bound using a spectrophotometer is characterized by performing the analysis using an inductively coupled plasma mass spectrometry (ICP-MS) or graphite furnace atomic absorption spectrophotometer.

DETAILED DESCRIPTION OF THE INVENTION

Figure 1:
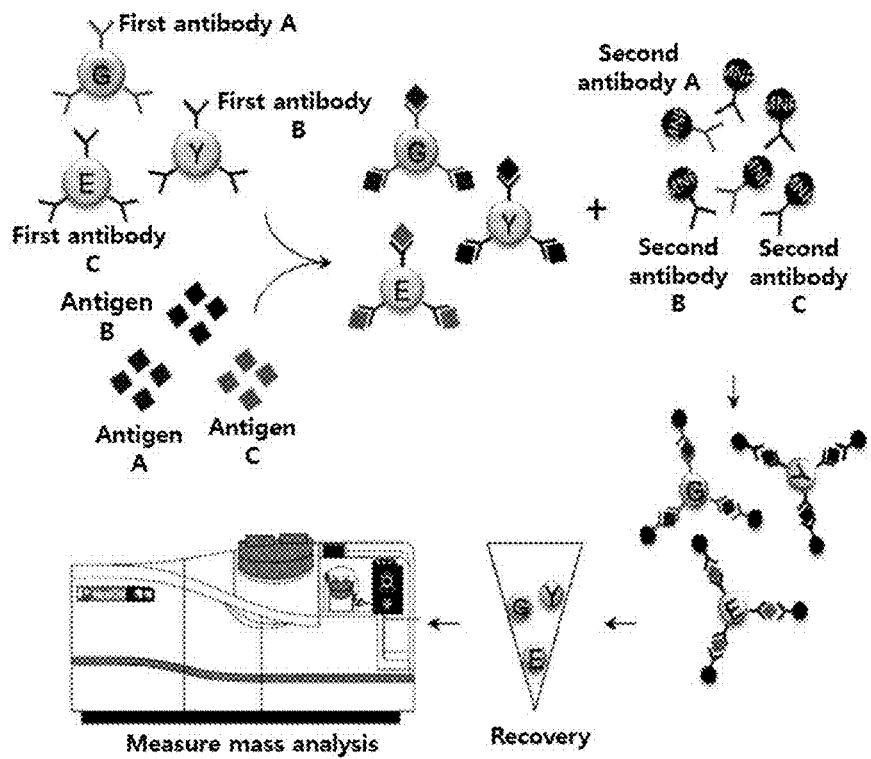
FIGS. 1 and 2 show schematic diagrams illustrating a method for simultaneous analysis of targets using a plurality of metal nano-tags by the present invention.
Figure 2:
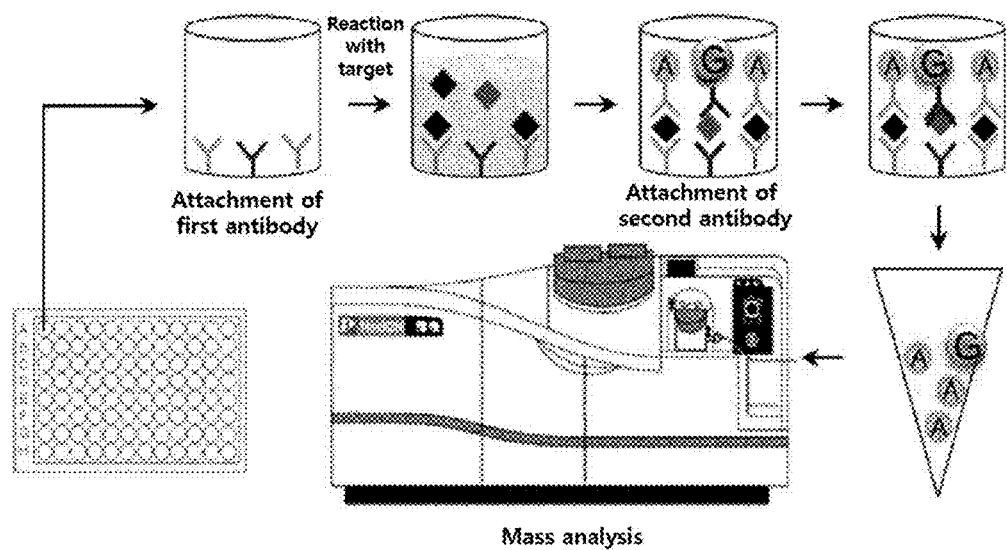

The method for simultaneous analysis of a plurality of targets using a plurality of metal nano-tags according to the present invention may include:

(i) preparing an analysis platform to which a first antibody, that specifically binds to a target, is bound;

(ii) reacting the analysis platform including the first antibody with a sample containing a plurality of targets and thereby forming an analysis platform to which target materials are bound;

(iii) reacting a second antibody, that specifically binds to a target, with the analysis platform in which the first antibody and targets are bound; and (iv) performing a quantitative analysis of the material to which the second antibody is bound.

In the method for simultaneous analysis of a plurality of targets using a plurality of metal nano-tags according to the present invention, the analysis platform to which the first antibody is bound may include a plurality of types of antibodies.

In the method for simultaneous analysis of a plurality of targets using a plurality of metal nano-tags according to the present invention, the analysis platform to which the first antibody is bound may be a silica nanoparticle which contains a magnetic metal-containing core and a silica that coats the surface of the core. The silica nanoparticle contains a single type of metal; and the analysis platform to which the antibody is bound contains at least two types of silica nanoparticles containing different types of metals. The metals contained in the silica nanoparticle may be selected from the group consisting of Au, Ag, Pt, Pd, Ir, Rh, Ru, Al, Cu, Te, Bi, Pb, Fe, Ce, Mo, Nb, W, Sb, Sn, V, Mn, Ni, Co, Zn, La, Ce, Pr, Nd, Pm, Sm, Eu, Gd, Tb, Dy, Ho, Er, Tm, Yb, Lu, Sc, Y, and Ti. The analysis platform to which the first antibody is bound may include at least two types of a plurality of types of silica nanoparticles selected from the group consisting of a silica nanoparticle containing a silica nanoparticle containing Au, a silica nanoparticle containing Gd, a silica nanoparticle containing Y, and a silica nanoparticle containing Eu. The second antibody may be bound to a silica nanoparticle, which contains a magnetic metal-containing core and a silica that coats the surface of the core.

In the method for simultaneous analysis of a plurality of targets using a plurality of metal nano-tags according to the present invention, the analysis platform to which the first antibody is bound may be a plate to which a plurality of types of the first antibody is bound.

In the method for simultaneous analysis of a plurality of targets using a plurality of metal nano-tags according to the present invention, the second antibody may be bound to a silica nanoparticle which contains a magnetic metal-containing core and a silica that coats the surface of the core.

In the method for simultaneous analysis of a plurality of targets using a plurality of metal nano-tags according to the present invention, the core of the silica nanoparticle bound to the second antibody may contain at least two metals selected from the group consisting of Au, Ag, Pt, Pd, Ir, Rh, Ru, Al, Cu, Te, Bi, Pb, Fe, Ce, Mo, Nb, W, Sb, Sn, V, Mn, Ni, Co, Zn, La, Ce, Pr, Nd, Pm, Sm, Eu, Gd, Tb, Dy, Ho, Er, Tm, Yb, Lu, Sc, Y, and Ti.

In the method for simultaneous analysis of a plurality of targets using a plurality of metal nano-tags according to the present invention, the core of the silica nanoparticle bound to the second antibody may contain Au.

In the method for simultaneous analysis of a plurality of targets using a plurality of metal nano-tags according to the present invention, the first antibody and the second antibody may be the same.

In the method for simultaneous analysis of a plurality of targets using a plurality of metal nano-tags according to the present invention, the first antibody may be a monoclonal antibody and the second antibody may be a polyclonal antibody.

In the method for simultaneous analysis of a plurality of targets using a plurality of metal nano-tags according to the present invention, step (iv) of performing a quantitative analysis of the material to which the second antibody is bound may include:

(iv-1) capturing the target material to which the second antibody is bound by applying an external magnetic force; and (iv-2) analyzing the captured target material to which the second antibody is bound using a spectrophotometer.

In the method for simultaneous analysis of a plurality of targets using a plurality of metal nano-tags according to the present invention, step (iv) of performing a quantitative analysis of the material to which the second antibody is bound may include:

(iv-1) separating the material, which is bound to the first antibody of the plate, to which the second antibody is bound; and (iv-2) analyzing only the material, which is bound to the first antibody of the plate, to which the second antibody is bound using a spectrophotometer.

In the method for simultaneous analysis of a plurality of targets using a plurality of metal nano-tags according to the present invention, step (iv-2) of analyzing the captured target material to which the second antibody is bound using a spectrophotometer may be to analyze using an inductively coupled plasma mass spectrometry (ICP-MS) or graphite furnace atomic absorption spectrophotometer.

EXAMPLES

Hereinafter, the present invention will be described in more detail with reference to examples. However, the present invention is not further limited by the following examples.

<Example 1> Case Using Plate as Analysis Platform Containing First Antibody

After attaching a Human anti-p24 monoclonal antibody as a first antibody to a plate, HBsAg was attached as a second antibody to the plate, and silica nanoparticles containing an Au particle were prepared using the Gold Nanoparticle Conjugation kit A blood sample was allowed to flow through the plate to induce a reaction between the first antibody and a target in the blood sample and unreacted impurities were removed by washing. The HBsAg was attached the resultant and allowed to react with a second antibody containing an Au particle.

Figure 3:
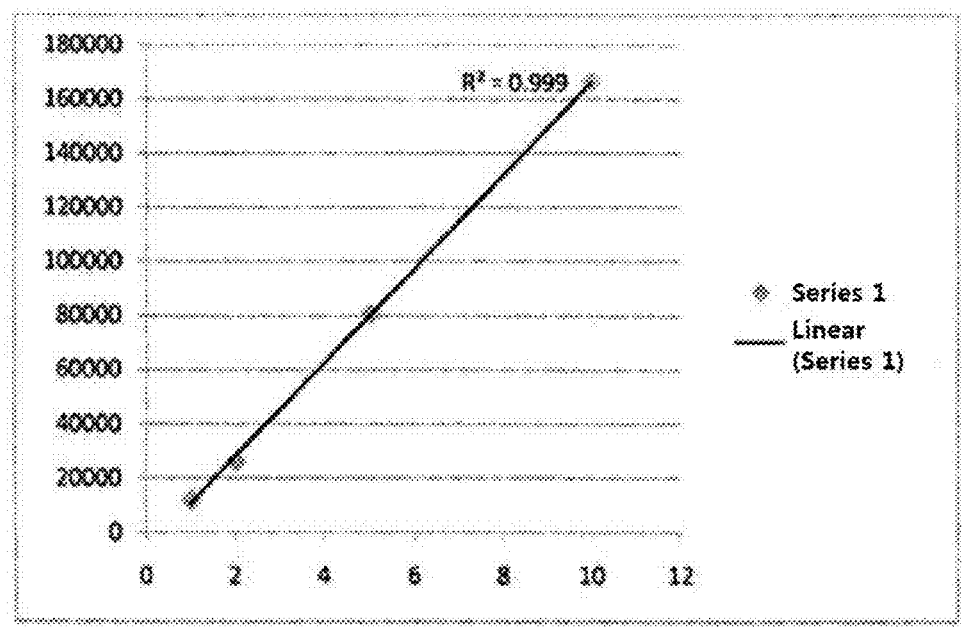
FIGS. 3 and 4 show the analysis results by ICP-MS in the blood according to an exemplary embodiment of the present invention.

Then, the conjugate bound to the second antibody was separated and recovered by a reaction with nitric acid and the weight of the conjugate was measured using an ICP-MS. The results are shown in FIG. 3.

<Example 2> Case Using Silica Nanoparticle as Analysis Platform Containing First Antibody Gadolinium-doped silica nanoparticles, yttrium-doped silica nanoparticles, and europium-doped silica nanoparticles were synthesized as an analysis platform containing the first antibody, respectively.

Human anti-p24 monoclonal antibody was attached to each of the synthesized silica nanoparticles as a first antibody and mixed, and thereby an analysis platform containing silica nanoparticles was prepared.

Iron nanoparticles were prepared as magnetic nanoparticles and by attaching human anti-p24 monoclonal antibody thereto as a second antibody.

Figure 4:
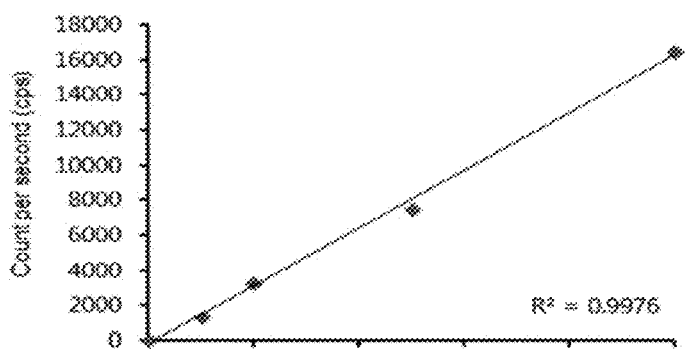
Figure 4:
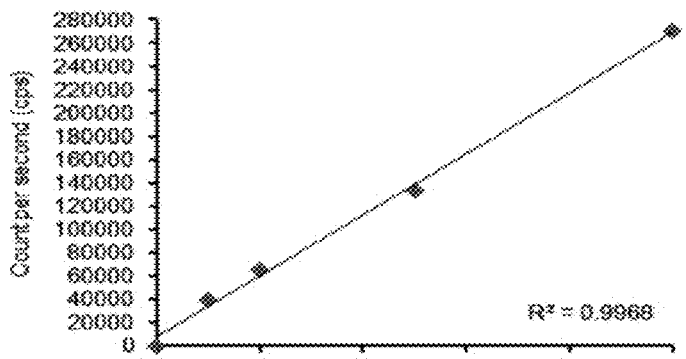

Silica nanoparticles, in which Gadolinium-doped silica nanoparticles, yttrium-doped silica nanoparticles, and europium-doped silica nanoparticles were mixed, were reacted with a sample containing target materials. After removing the unreacted materials, the conjugate bound to the second antibody was separated and recovered by a reaction with nitric acid, and the weight of the resultant was measured by ICP-MS. The results are shown in FIG. 4.

It was confirmed that a plurality of targets can be quantitatively analyzed when a method for simultaneous analysis of a plurality of targets using a plurality of metal nano-tags according to the present invention.

ADVANTAGEOUS EFFECTS OF INVENTION

The analysis method for a target material using metal nano-tags according to the present invention fuses a nanotechnology to a conventional biological immune response, and the method thereby makes it possible to accurately detect even a trace amount of virus without the burden of inspection cost, in the business of verification/diagnosis of blood preparations, viruses, and other biomedicines as well as in the blood management business which deals with a large amount of blood samples.

The invention claimed is:

1. A method for simultaneous analysis of a plurality of targets in a blood sample using a plurality of metals, comprising: (i) preparing a first analysis platform to which a first antibody, that specifically binds to a target, is bound; (ii) reacting the first analysis platform comprising the first antibody with a blood sample comprising a plurality of targets and thereby forming a second analysis platform to which target materials are bound; (iii) reacting a second antibody, that specifically binds to a target, with the second analysis platform in which the first antibody and targets are bound; and (iv) performing a quantitative analysis of the target material to which the second antibody is bound; wherein the first analysis platform to which the first antibody is bound is silica nanoparticles, and comprises a plurality of types of first antibodies, wherein the silica nanoparticles have a metal-comprising core and silica that coats the surface of the core, wherein the targets analyzed are targets in blood samples and comprise at least two selected from the group consisting of hepatitis B virus (HBV), hepatitis C virus (HCV), and human immunodeficiency virus (HIV), wherein the first analysis platform to which the first antibody is bound comprises at least two types of silica nanoparticles containing different types of metals, wherein the silica nanoparticle comprises Au (gold) when the target to be analyzed is HBV, the silica nanoparticle comprises Gd (gadolinium) when the target to be analyzed is HIV, and the silica nanoparticle comprises Eu (europium) when the target to be analyzed is HCV.

2. The method of claim 1, wherein the first antibody and the second antibody are the same.

3. The method of claim 1, wherein the first antibody is a monoclonal antibody and the second antibody is a polyclonal antibody.

4. The method of claim 1, wherein step (iv) of performing a quantitative analysis of the target material to which the second antibody is bound comprises:

(iv-1) capturing the target material to which the second antibody is bound by applying an external magnetic force; and (iv-2) analyzing the captured target material to which the second antibody is bound using a spectrophotometer.

5. The method of claim 4, wherein step (iv-2) of analyzing the captured target material to which the second antibody is bound using a spectrophotometer comprises analyzing by using an inductively coupled plasma mass spectrometry (ICP-MS) or graphite furnace atomic absorption spectrophotometer.

* * * * *